United States Patent
Schardey

(10) Patent No.: US 10,368,812 B2
(45) Date of Patent: Aug. 6, 2019

(54) SYSTEM FOR THE EARLY DETECTION OF LIFE-THREATENING CONDITIONS OF PERSONS

(75) Inventor: Anne Schardey, Gmund (DE)

(73) Assignee: ISAR-M GmbH Medical Technology, Holzkirchen (DE)

( * ) Notice: Subject to any disclaimer, the term of this patent is extended or adjusted under 35 U.S.C. 154(b) by 757 days.

(21) Appl. No.: 13/699,412

(22) PCT Filed: Apr. 18, 2011

(86) PCT No.: PCT/EP2011/056113
§ 371 (c)(1),
(2), (4) Date: Feb. 11, 2013

(87) PCT Pub. No.: WO2011/131612
PCT Pub. Date: Oct. 27, 2011

(65) Prior Publication Data
US 2013/0137941 A1    May 30, 2013

(30) Foreign Application Priority Data

Apr. 19, 2010  (EP) .................................... 10160370

(51) Int. Cl.
*A61B 5/00* (2006.01)
*A61B 5/024* (2006.01)
(Continued)

(52) U.S. Cl.
CPC .......... *A61B 5/7282* (2013.01); *A61B 5/0004* (2013.01); *A61B 5/021* (2013.01);
(Continued)

(58) Field of Classification Search
CPC .. A61M 1/3635; A61M 1/3656; G01N 33/49; G06F 19/34; A61B 5/02042
(Continued)

(56) References Cited

U.S. PATENT DOCUMENTS

| | | | |
|---|---|---|---|
| 2004/0143174 A1* | 7/2004 | Brubaker | G01N 33/4905 600/369 |
| 2005/0187796 A1* | 8/2005 | Rosenfeld | G06F 19/325 705/3 |
| 2007/0238995 A1 | 10/2007 | Sui et al. | |
| 2008/0146895 A1 | 6/2008 | Olson et al. | |

(Continued)

OTHER PUBLICATIONS

International Search Report dated Jan. 17, 2012 in PCT/ EP11/ 56113 Filed Apr. 18, 2011.

(Continued)

*Primary Examiner* — Boniface N Nganga
(74) *Attorney, Agent, or Firm* — Oblon, McClelland, Maier & Neustadt, L.L.P.

(57) ABSTRACT

The invention relates to a system for the early detection of life-threatening conditions of persons, wherein such risks exist, for example, due to a preceding operation. The system detects a plurality of vital parameters depending on the person to be monitored by means of a detector unit that is subsequently evaluated by an evaluation logic using a neuronal network. Individual parameters that exceed thresholds and constellations of parameters that represent a critical health condition of the person are displayed in different forms by means of a display device, depending on the risk. Said risk is determined in that the probability of the presence of a health anomaly is first determined and then evaluated.

17 Claims, 4 Drawing Sheets

(51) Int. Cl.
*A61B 5/11* (2006.01)
*A61B 5/145* (2006.01)
*A61B 5/03* (2006.01)
*A61B 5/0205* (2006.01)
*A61B 5/021* (2006.01)
*A61B 5/08* (2006.01)
*G16H 50/20* (2018.01)
*G16H 50/30* (2018.01)

(52) U.S. Cl.
CPC ............ *A61B 5/024* (2013.01); *A61B 5/0205* (2013.01); *A61B 5/03* (2013.01); *A61B 5/0816* (2013.01); *A61B 5/1112* (2013.01); *A61B 5/1113* (2013.01); *A61B 5/14542* (2013.01); *A61B 5/7267* (2013.01); *A61B 5/7275* (2013.01); *A61B 5/742* (2013.01); *G16H 50/20* (2018.01); *G16H 50/30* (2018.01)

(58) Field of Classification Search
USPC ........................................................ 600/371
See application file for complete search history.

(56) References Cited

U.S. PATENT DOCUMENTS

| | | | |
|---|---|---|---|
| 2008/0167567 A1 | 7/2008 | Bashour et al. | |
| 2008/0287753 A1* | 11/2008 | Parlikar ................. | A61B 5/021 600/301 |
| 2009/0326339 A1* | 12/2009 | Horvitz ......................... | 600/301 |
| 2010/0234695 A1* | 9/2010 | Morris .......................... | 600/300 |
| 2010/0268096 A1* | 10/2010 | Berka ................ | A61B 5/02433 600/485 |
| 2011/0133927 A1* | 6/2011 | Humphrey et al. ..... | 340/539.11 |
| 2011/0160549 A1* | 6/2011 | Saroka .................... | A61B 5/00 600/301 |
| 2011/0282169 A1* | 11/2011 | Grudic ................ | G06F 19/3437 600/324 |
| 2012/0330117 A1* | 12/2012 | Grudic ............... | A61B 5/02028 600/324 |

OTHER PUBLICATIONS

Extended European Search Report dated Feb. 21, 2011 in Patent Application No. 10160370.2 with English translation of categories of cited documents.

* cited by examiner 3A  3B

SYSTEM FOR THE EARLY DETECTION OF LIFE-THREATENING CONDITIONS OF PERSONS

The invention relates to a system for early detection of life-threatening conditions of persons.

Monitoring systems are known in various designs, which are preferably used in hospitals for patient monitoring. They monitor only relevant vital parameters, such as pulse, heart rate, etc. and trip an alarm if the respective static limit values of the vital parameters are exceeded. In the course following surgery, however, it is possible for various complications such as shock, cardiac infarction, pulmonary embolism and bleeding to occur, and these cannot be made noticeable by a trivial exceedance of a limit value of individual vital parameters.

In the case of bleeding, it is important that non-significant hematomas be distinguished from internal post-bleeding, in order to detect the danger of hemorrhaging or of compression of vital organs. The problem of postoperative bleeding is particularly significant against the background that a tonsillectomy among other surgeries is the most frequently performed routine surgical procedure in the ENT region, where the most frequent complication after such surgery is post-bleeding. Especially children, who frequently die as a result of undetected post-bleeding, are particularly at risk because of good body compensation, poor ability to communicate and their tendency to panic and become agitated.

The danger also exists of compression of vital organs, such as the trachea, as a result of post-bleeding. In Germany, post-bleeding is recorded in approximately 800 cases of thyroid surgery each year, as a result of which approximately 16 patients die and almost as many more patients lapse into a persistent vegetative state. Since the aforesaid dangers cannot be detected reliably and early enough with the conventional types of monitoring, action toward further development of current systems is needed.

The object of the invention is therefore to provide a system that is particularly suitable for detecting life-threatening conditions of persons.

With regard to the system for early detection of life-threatening conditions of persons, this object is achieved by the features of claim 1.

The inventive system for early detection of life-threatening conditions of persons is capable of simultaneously processing several vital parameters of a person to be monitored. These vital parameters are fed, preferably continuously, by a detector unit, which may consist of measuring sensors and a computing unit as well as an interface, to an evaluation logic, with which the recorded parameters are assigned various predetermined conditions and an assessment of the probability of existence of a health anomaly is made as a function of the existing parameter conditions. The inventors have found that, if an appropriate selection of the vital parameters to be monitored is made and if the measured parameters are appropriately classified in the conditions to be queried, the automatically operating system is immediately able to ascertain a probability as to the condition of the person to be monitored, thus permitting a clear distinction between life-threatening conditions on the one hand and basically uncritical conditions on the other hand. An essential consideration in this respect is the knowledge that, by using an evaluation logic that operates not digitally but instead with intermediate criteria, it is possible, even in the case of relatively few parameters to be monitored, to distinguish life-threatening conditions from normal conditions. The mode of operation of the system not only can be refined as desired via the number of vital parameters and/or the number of conditions assigned to the measured parameters, but also can be adapted to the respective individual response patterns of the persons to be monitored. The display device with which the assessment is displayed is advantageous, because on the one hand it may be used to alert the person to be monitored to a condition that is critical for him or her, and at the same time it may be used to communicate the result of the evaluation, for example to a hospital or to a treating physician, in such a way that life-saving measures can be initiated as soon as possible. It has been found that, for example by monitoring only five vital parameters and assigning these vital parameters to only five conditions or categories, it is possible to distinguish postoperative bleeding reliably from harmless health conditions, especially when these conditions are matched individually to the person to be monitored. Furthermore, the evaluation logic is provided with a neuronal network, by means of which parameter patterns trained in advance can be detected.

Advantageous improvements are subject matter of the dependent claims.

Advantageously, the early detection system, with the assistance of the evaluation logic, is additionally capable of generating, on the basis of the recorded vital parameters and parameter conditions, especially when the chronology of the course is taken into consideration, an instruction of the way in which the person to be monitored must be treated. This therefore corresponds to an individual recommendation of action, adapted to the circumstances, either for the person to be monitored himself or herself or for third parties, for example for a treating physician or for a first aider, who finds the person to be monitored in a critical condition. Since this recommendation of action is automatically generated as a function of the recorded parameter set, it may be assessed even if the person to be monitored is no longer capable of providing any information at all. Accordingly, in an emergency situation, valuable time can be gained between the diagnosis and the start of treatment.

Depending on the type of display device, the instruction may be displayed at least in part. This primarily enables the person to be monitored to estimate his or her own condition and to stop worrying unnecessarily if the condition is not life-threatening. Otherwise, the instruction in the case of a life-threatening condition may indicate among other messages that an emergency physician is to be informed immediately. At the same time, specific instructions as to how the person must be treated may also be displayed. In this way, for example, the arriving physician can immediately begin the correct treatment. This achieves a great time savings, since neither does that physician have to examine the person to be monitored nor must additional time be spent to find the diagnosis. Furthermore, since the early detection system knows the medical history of the person to be monitored, the instruction of the system corresponds to that which a family doctor familiar with the medical history would order. Should special equipment that does not belong to the equipment normally brought along by emergency physicians be necessary for treatment of the person to be monitored, precious time can again be gained by an instruction containing information about this circumstance.

In principle, any unit capable of recording the selected vital parameters can function as the detector unit. If the detector unit is equipped with measuring sensors and possibly a computing unit as well as possibly an interface, the system is constructed in such a way that it can be worn as a body-fitting, compact system on the body of the person to be monitored. The computing unit converts the input signal of the measuring sensors in such a way that it is visible, for example on an external instrument via an interface. The advantage of the interface is that on the one hand the vital parameters of the person to be monitored can be made quickly visible in an emergency for a specialist, such as a physician, and that on the other hand the system can be read with very little effort for routine controls.

The inventive system monitors all relevant vital parameters and assigns a predefined condition to them. By means of a neuronal network according to claim 4, the evaluation logic is further capable of handling the large number of parameter sets rapidly and identifying any life-threatening conditions without delay. Furthermore, certain parameter sets determined by clinical research can be communicated to the neuronal network by means of training. Thereby an even more accurate distinction between a non-significant and a life-threatening condition can be made for the parameter sets.

By recording the vital parameters at preset time intervals (dt), which preferably are adapted to the health condition of the patient, it is possible to use the system in particularly energy-saving manner, thus achieving a long operating time.

The system is particularly attractive because of the variable time intervals (dt) for recording the vital parameters. This feature permits the system to vary the intervals between two measured points as a function of the circumstances, so that the time intervals can be adapted to the current health condition of the patient during operation of the system. As an example, they become shorter if the condition worsens and longer if the condition improves. In this way the time intervals (dt) can also be made longer during uncritical phases, such as during sleep, in order again to permit an energy-saving mode of operation.

By virtue of the further improvement of claim 6, in which the evaluation logic is based on a fuzzy logic algorithm instead of the customary binary digital algorithm, the vital parameters do not necessarily have to be assigned to one of two possible opposite conditions, but instead even to any desired intermediate values, thus enhancing the working accuracy of the system and increasing the number of detectable conditions of the person to be monitored.

The better the system is adapted to the patient, the more effectively and more accurately it is able to operate. Therefore it is advantageous for the system to be trained with individual medical data of the person to be monitored. In this way the system is able to distinguish even more accurately between a critical health condition and uncritical conditions such as a resting phase or brief stress phase, especially when the measured parameters differ considerably from person to person. This distinction has the consequence that considerably fewer false alarms are displayed or reported.

By virtue of the improvement presented in claim 8, the fuzzy logic module of the evaluation logic can be individually calibrated beforehand to correspond to the health condition of the person to be monitored. Thereby some adaptation runs at the beginning of service are obviated and the patient is monitored as well as possible from the beginning.

In order to improve the system continuously during service and to adapt it to the individual conditions of the patient during its service life, the evaluation logic can be designed with learning capability. This has the advantage that the system is able to adapt during service to habits and rhythms of the patient during operation. Thereby individual vital parameters and their relationships with one another are recorded, once again making it possible to obtain more accurate information about non-significant conditions, such as sleep phases or short periods of effort, as compared with life-threatening conditions, such as postoperative bleeding.

When an assessment of the probability of the existence of a health anomaly according to claim 10 is displayed, the result of monitoring can be very easily understood. In this case the display unit has the option of signaling various levels of the health danger, for example optically by means of different colored signal lights. This permits a better estimate of the tripped alarm, since a life-threatening condition can be clearly displayed differentially compared with values that are merely slightly elevated. This in turn prevents unnecessary anxiety of the patient, thus ultimately avoiding further deterioration of the health condition. In addition, false alarms and costs resulting unnecessarily from them are avoided.

By virtue of the improvement of claim 11, at least one selected result of the assessment and/or one instruction about how to deal with the momentary condition of the person to be monitored can be communicated by a transmitter unit to a control room. In this way corresponding specialists will be able to analyze the result of the assessment immediately and take any appropriate action.

In order to be able to identify the spatial or geographic position of the person to be monitored, the transmitter unit can be equipped with a position detector. This is designed in such a way that can identify the position of the person to be monitored, preferably continuously.

The transmitter unit may be designed such that it communicates the particular spatial or geographic position of the person to be monitored to a control room. Consequently the person to be monitored can be located immediately if a life-threatening condition has occurred, even if that person is not independently capable of making himself or herself noticeable. In this way valuable time can be gained in locating the place of a stationary or even a non-stationary patient.

Furthermore, the system of claim 1 may be equipped with an interface that permits a connection to a mobile telephone. On the one hand, the mobile telephone allows a position to be identified even in places where conventional systems, such as GPS, do not work, and on the other hand the mobile telephone can be used to communicate information.

The system is particularly practical and easy to start up when all of its components are combined in one instrument. This has the consequence that this system can be purchased commercially as a unit for anyone and can be used without requiring any assembly. Furthermore, the system can be designed as a wireless unit, making it particularly easy for the user to wear it on the body, for example on the wrist, belt or the like.

An exemplary embodiment of the invention will be explained in more detail hereinafter with reference to schematic drawings, wherein.

Figure 1:
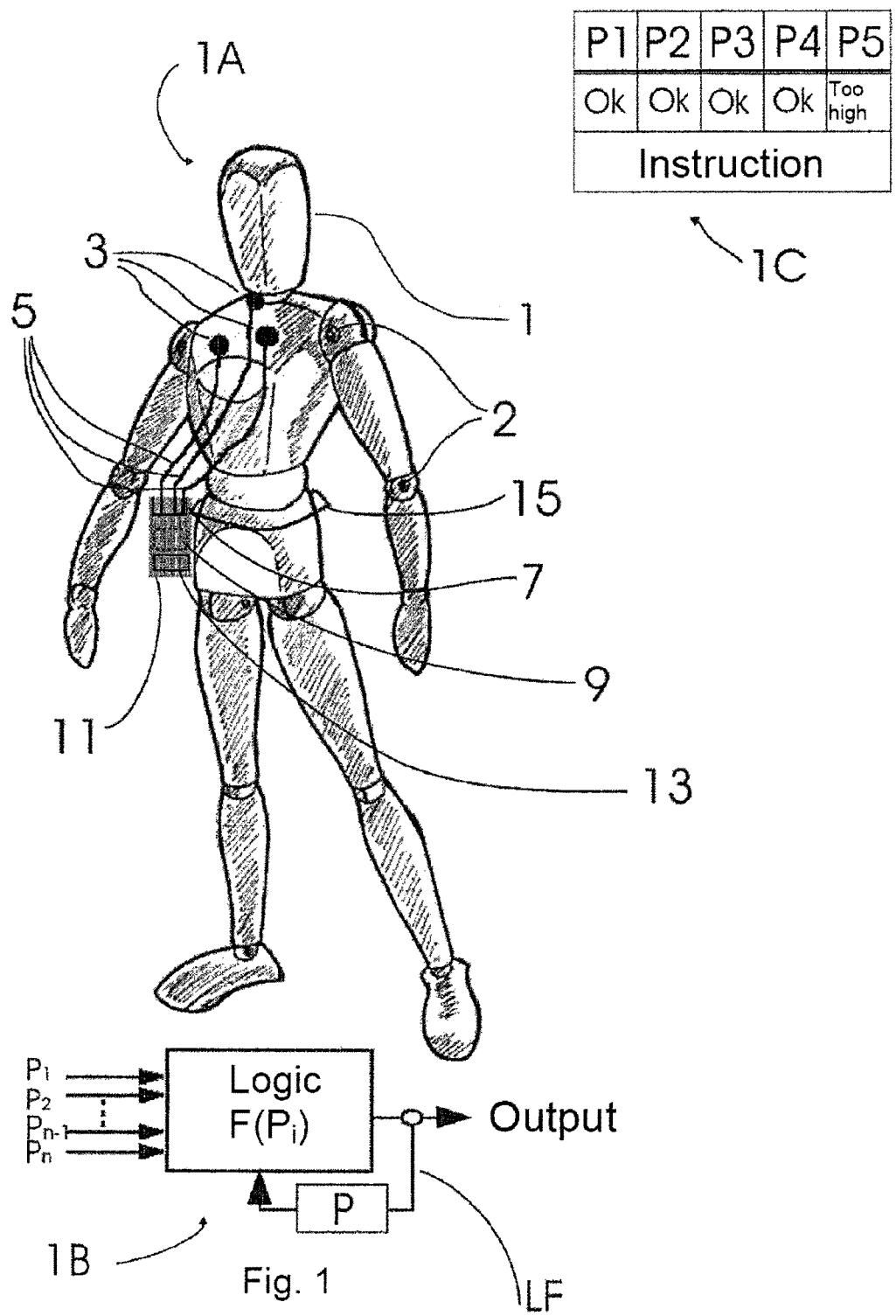
FIGS. 1A to 1C show a schematic diagram of the system for early detection of life-threatening conditions, which system will be worn by a person to be monitored, a block diagram of the evaluation logic and further variants of displays.

In FIG. 1A, a person to be monitored (referred to hereinafter as person) is schematically denoted by reference numeral 1. Here the places marked with reference numeral 2 denote joints.

To record the vital parameters, measuring sensors 3, which are represented by solid circles, are attached to the person. Depending on vital parameters, measuring sensors 3 are attached to different sites of the body of person 1. In the illustrated exemplary embodiment, data transmission takes place via a cable 5, but wireless data transmission by infrared or radio techniques is also possible. Cables 5 are connected at their one end to measuring sensor 3 and at their other end to an interface 7. From interface 7, the vital parameters recorded by measuring sensors 3 travel to an electronic control unit (ECU) 9, which together with elements 3, 5 and 7 just mentioned forms the detector unit, which in turn is completely received in a housing 11.

In the detector unit, interface 7 performs two functions. On the one hand it serves as a kind of internal interface of the detector unit for the vital parameters recorded by measuring sensors 3. On the other hand interface 7 serves as an external interface, to which external instruments, such as a computer or monitor, can be connected.

Furthermore, housing 11 contains ECU 9 of the detector unit. It is equipped with a clock generator and therefore executes all computing processes. Depending on vital parameters and condition of the person to be monitored, the time intervals between two measurement points may differ greatly from one another. For example, whereas measurements of the heart rate must be made at much shorter time intervals from one another in order to detect a life-threatening situation early and quickly, measurements concerning the oxygen saturation of the blood are sufficient even at longer intervals.

Furthermore, ECU 9 may be designed in such a way that it is able to access a memory in which there are stored all relevant instructions on how the person to be monitored must be handled as a function of the momentarily existing vital parameters. This memory may be both an internal and an external memory. Therein ECU 9 is able to store both the instructions, so that they can be read out as needed, and also courses or evolutions of courses of vital parameters over prolonged time periods. As an example, these may be read out and analyzed via interface 7 for routine controls.

The sequence presented in the following is described by the block diagram illustrated in FIG. 1B, wherein the input variables are denoted by $P_1$ to $P_n$, the evaluation logic by $F(P_i)$, the feedback path for learning capability by LF and the processing of the result for adaptation of the evaluation logic for future evaluations by P. Depending on treatment situation, the recorded vital parameters are fed to ECU 9, which then assigns them to various predefined conditions, such as very low, low, normal, high and very high on the basis of a fuzzy logic algorithm.

Thereupon the evaluation logic undertakes an assessment of the probability of the existence of a health anomaly as a function of the existing parameter set. In this process the probability of postoperative bleeding, for example, may be output as a result, and likewise that of thrombosis, embolism, etc. may be assessed. After the assessment has been obtained, it is displayed with a display unit 13, if deemed necessary by the logic.

Together with the assessments, instructions may be output at display device 13, which instructions may be read partly, continuously or by means of symbols, depending on display device 13. In display devices 13 that tend to be smaller, the instructions can be displayed only partly, whereas a larger display device 13 also permits the display of more detailed instructions. For an operating situation in which only a particularly small display device 13 is possible, assessments such as illustrated in FIG. 1C can be reproduced by means of unambiguous symbols or by a combination of symbols and texts. In this case the top row shows the recorded vital parameters and the middle row shows the respective assessments. The bottom row may be blank or display the notice that all values are uncritical, provided no danger exists for the person to be monitored. If a critical condition is ascertained, an instruction may appear, flash or scroll in this text field. Furthermore, different vital parameters may be displayed in alternation in the columns, as long as no critical values are recorded.

As examples, individual instructions may read as follows:
Important: Postoperative bleeding suspected (date of surgery XX.XX.XXXX); call physician immediately!
Oxygen concentration too low. Consult your doctor at tel.: . . . . . . . . . . ;
Attention: Pulse rate high. Please begin rest period!

Furthermore, since vital parameters may differ considerably from one another depending on the momentary activity of the person, the result of the evaluation logic is further fed back to it via processing step P. In this way the system learns to distinguish possible uncritical conditions, such as rest conditions, better from critical conditions.

Figure 2:
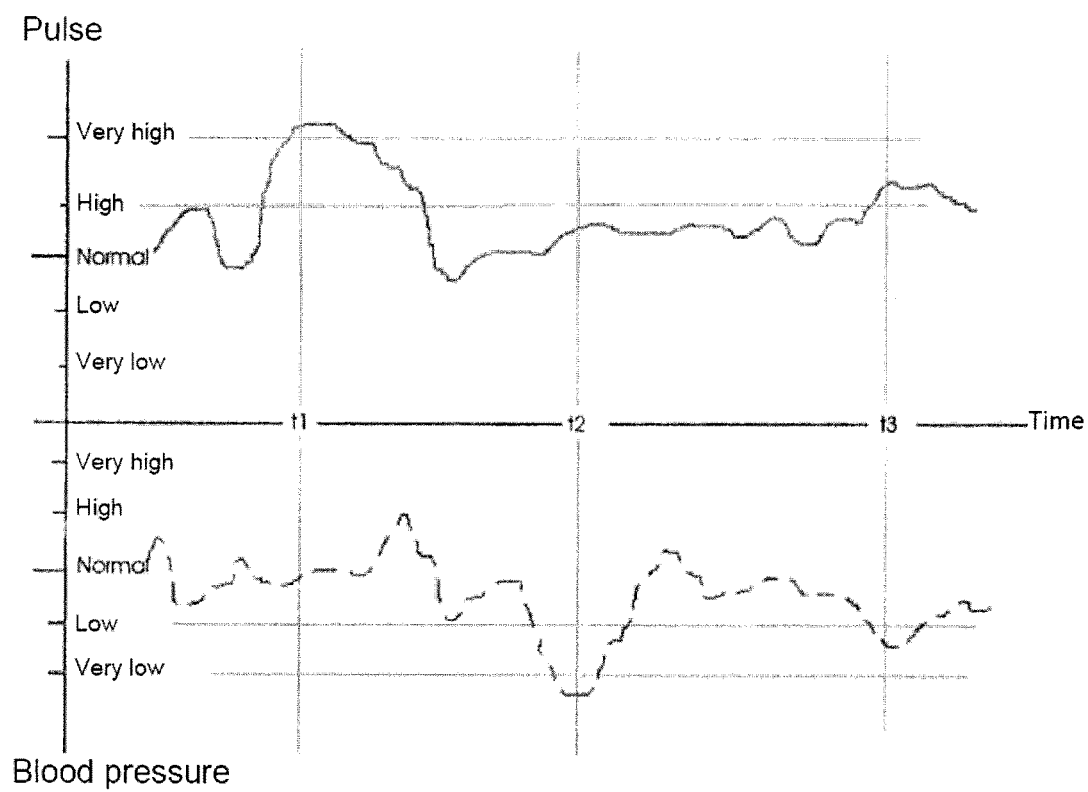
FIG. 2 shows variations in time of two vital parameters, the exceedance of a limit value of which at certain instants respectively trips an alarm.

Examples of variations in time of two vital parameters are shown in FIGS. 2A and 2B. The abscissa corresponds to the time axis, along which three different instants (t1, t2, t3) are plotted as examples. Along the ordinate, the conditions for the pulse (solid line) are plotted at the top and the conditions for the blood pressure (broken line) are plotted at the bottom. The two instants t1 and t2 respectively correspond to a limit-value exceedance above a maximum permissible value for the respective vital parameter. Thus at instant t1 the pulse exceeds the upper limit value specified for it and is assigned to the condition of very high. At instant t2 the blood pressure falls below the lower limit value specified for it and is assigned to the condition of very low. In both cases, the evaluation logic trips an alarm, in order to signal a life-threatening condition of person 1.

In contrast, a different situation exists at instant t3. In contrast to the two preceding cases, no limit value is exceeded here but instead the fuzzy logic detects that abnormally high values have occurred for two vital parameters. On the basis of the parameter set, a probability for a diagnosis is calculated and assessed by a learning-capable neuronal network of the evaluation logic.

Figure 3:
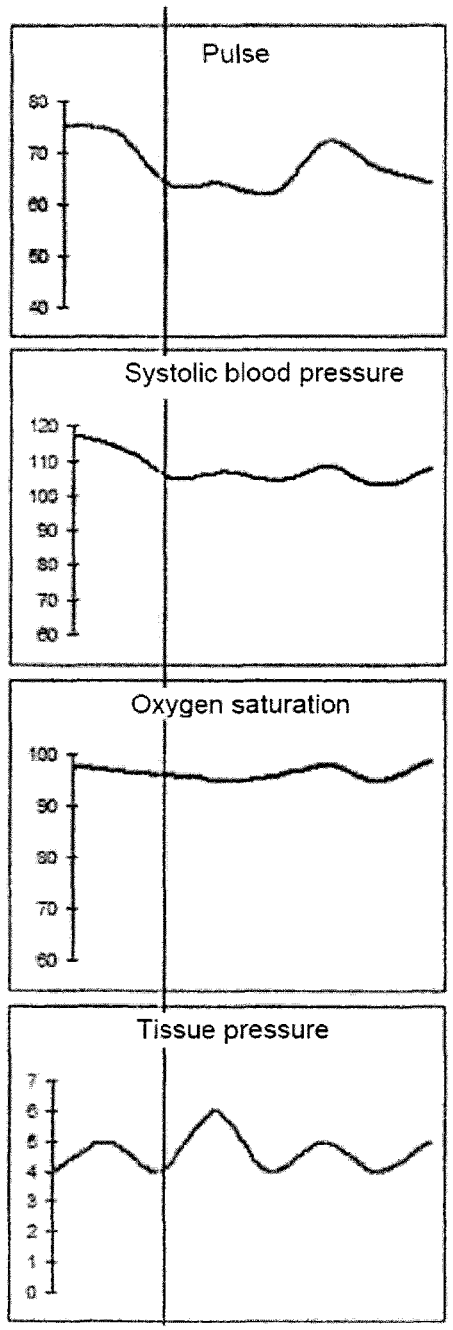
FIGS. 3A and 3B show two possible parameter sets, for sleep and agitation, of a person to be monitored.
Figure 3:
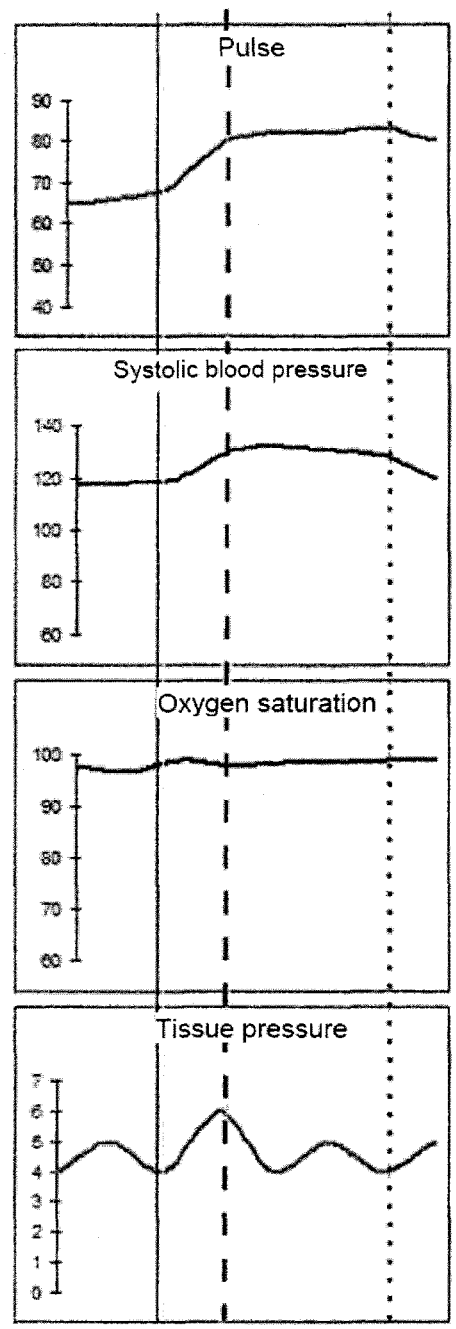

FIGS. 3A (left column) and 3B (right column) show the set of four parameters for the cases of sleep and agitation as examples. From top to bottom, the left four fields of FIG. 3A show the variations of pulse, systolic blood pressure, oxygen saturation and tissue pressure. Each of these cited values is plotted on the ordinate, while the abscissa corresponds to the passage of time. The occurrence of an event is represented by a solid vertical line.

From the beginning of the sleep phase, variations in the course of the vital parameters are detectable on the one hand in the distinctly slowing pulse and on the other hand in the dropping systolic blood pressure. The other two vital parameters, oxygen saturation and tissue pressure, remain almost constant. The neuronal network unequivocally interprets this parameter set as a sleep phase and accordingly does not trip any alarm on the display device.

The four fields of FIG. 3B correspond to those of FIG. 3A, but in this case the parameter set of agitation is illustrated. As before, the occurrence of an event is represented by a solid vertical line. The dashed vertical line represents a first alarm. This means that a critical parameter set has been detected and a diagnosis is necessary in order to avoid a life-threatening condition. In the cited example, the pulse has become much faster, while the systolic blood pressure has also risen almost synchronously. In the two lower plots, almost no change has occurred. Accordingly, agitation is detected in the person. When the plots are considered at an even later time (vertical dotted line), both the pulse and the systolic blood pressure exhibit a dropping trend, which in the totality of the vital parameters under consideration indicates normalization of the condition of the person. This is represented by a vertical dotted line, which proves that the early detection system is working flawlessly and the person is in an uncritical condition.

Figure 4:
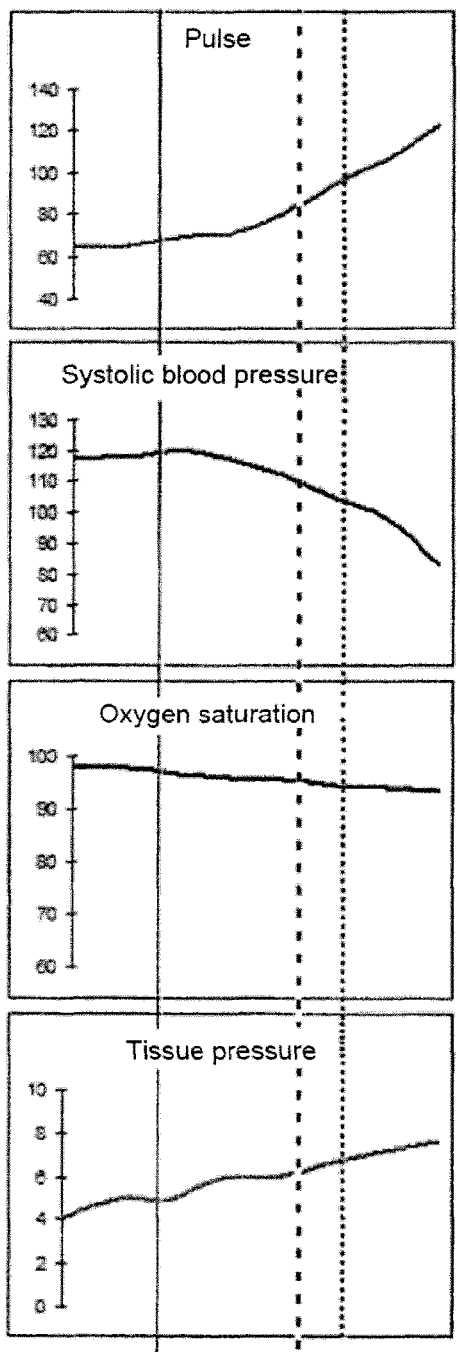
FIGS. 4A and 4B show two possible parameter sets, for bleeding in a body cavity and bleeding in the surgical site, of a person to be monitored.
Figure 4:
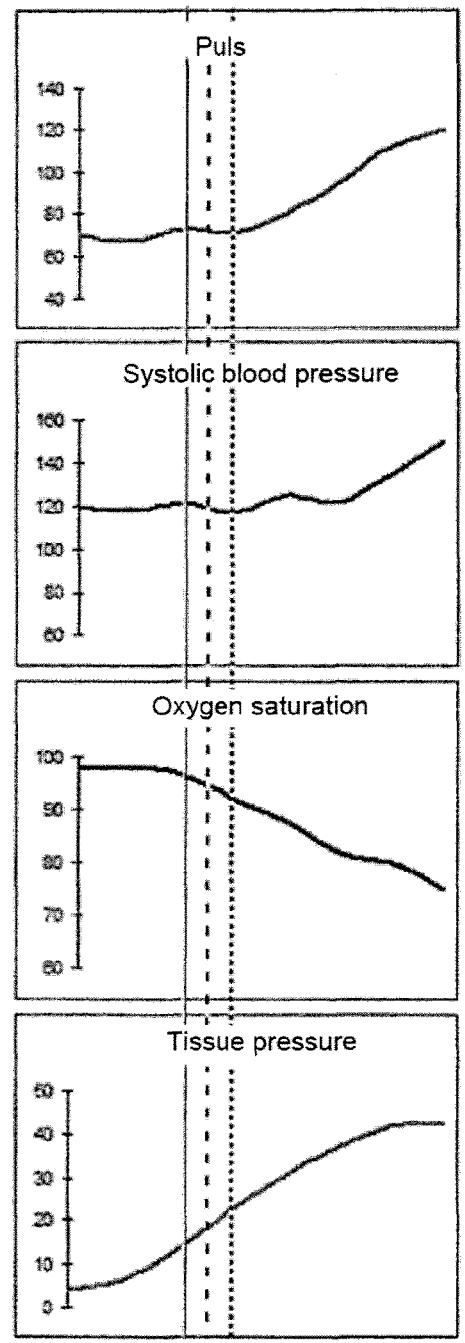

Two further possible parameter sets are illustrated in FIGS. 4A (left column) and 4B (right column). In FIG. 4A, changes of three vital parameters can be detected after occurrence of an event (represented by the vertical solid line). Whereas the pulse rate rises, slightly at first then increasingly more strongly, the systolic blood pressure drops. In parallel, the tissue pressure rises while the oxygen saturation remains almost constant. In the combination of these three vital parameters, the first alarm indicating the need for a diagnosis is tripped at the vertical dashed line.

In the parameter set just described, the display device would display a notice about bleeding in a body cavity. Since none of the plots becomes re-normalized, but instead all continue to deteriorate, an emergency alarm is tripped at the vertical dotted line. This indicates that treatment is required immediately, since the person is in a life-threatening condition.

FIG. 4B represents a further parameter set, in which all four vital parameters under consideration show an altered course after the occurrence of an event (represented by the vertical solid line). Immediately after the event, the oxygen saturation begins to decrease on the one hand while the tissue pressure begins to rise on the other hand. Since the values of these two parameters rapidly reach critical values (represented by the vertical dashed and subsequent vertical dotted lines), the first alarm and then the emergency alarm for a life-threatening condition are tripped by analogy with the two mentioned lines.

Obviously deviations from the exemplary embodiments described in the foregoing are possible without departing from the fundamental ideas of the invention.

For example, it is equally possible to attach the measuring sensors at any other part of the body that is suitable for recording the respective vital parameters. Likewise the measuring sensors are not subject to any restriction on their shape or size.

It is obviously also possible to communicate the recorded signals of the measuring sensors to the system in a different way, for example wirelessly by means of an infrared or radio link.

Furthermore, it is conceivable that the system does not necessarily have to be worn on the person's hip and that it may also be hung around the neck or worn on the arm or leg.

Various modifications of the display device are conceivable, wherein the levels of the health danger can be displayed. A kind of traffic-signal display using the three colors green, yellow and red is just as conceivable as a display that shows bars or other elements of various sizes.

Aside from the fact that the person to be monitored carries the system with him or her, it may also be kept at a different location, for example with the treating physician, in a hospital or in another monitoring station set up specifically for this purpose.

Limit-value exceedances of vital parameters other than pulse and heart rate may also lead to tripping of the alarm, for example heart rate, respiration rate, blood oxygen concentration, tissue pressure, etc. Likewise an altered EKG, which suggests an acute heart disease such as a cardiac infarction, may lead to tripping of the alarm.

Obviously parameter sets other than merely those shown here may lead to tripping of an alarm. The system may be trained in all parameter sets that are known and relevant for the person to be monitored, and accordingly these may be detected by the system.

Aside from the applications described hereinabove, the system of the present invention may also be employed for wellness purposes. For example, the instrument could also provide older leisure and extreme athletes the safety of health monitoring.

The invention therefore creates a system for early detection of life-threatening conditions of persons, in whom such risks exist, for example, because of previous surgery. Depending on the person to be monitored, the system records several vital parameters via a detector unit, which parameters are then evaluated by an evaluation logic, preferably using a neuronal network. Depending on the danger, on the one hand limit value exceedances of individual parameters and on the other hand parameter sets that represent a condition critical to the health of the person are then displayed in various forms with a display device. It is designed first to determine and then to assess the probability of the existence of a health anomaly.

The invention claimed is:

1. A system that detects the probability of post-operative bleeding in a person, comprising:
    a detector unit that records a plurality of vital parameters, wherein the detector unit comprises at least one measuring sensor, an electronic control unit assisted by a computing unit, and an interface, wherein the said detector unit records blood pressure, heart rate of the person and one or more vital parameters of the person selected from the group consisting of:
    (a) oxygen content of blood, and
    (b) tissue pressure;
    wherein said electronic control unit executes an evaluation logic embodied in a computer-readable medium and assigns a predefined condition to each vital parameter measured by the at least one measuring sensor, and assesses a probability of post-operative bleeding as a function of the assigned predefined conditions, wherein the evaluation logic generates, based on medical history of the person, the recorded parameters, and the assigned conditions, taking into consideration their variation in time, an instruction on how to deal with the predicted post-operative bleeding and equipment necessary to deal with the predicted post-operative bleeding; and
    a display device which receives from the detector unit via the interface the probability of post-operative bleeding from the computing unit and displays the probability of post- operative bleeding and the instruction.

2. The system of claim 1, wherein the evaluation logic comprises a neuronal network.

3. The system of claim 1, wherein the detector unit records at least one of the vital parameters at a predefined time interval.

4. The system of claim 1, wherein the evaluation logic comprises a fuzzy logic algorithm.

5. The system of claim 2, wherein the neuronal network is trainable by incorporating individual medical data of the person.

6. The system of claim 4, wherein the fuzzy logic algorithm of the evaluation logic is individually calibrated in a manner corresponding to the health of the person.

7. The system of claim 1, wherein the evaluation logic is capable of learning.

8. The system of claim 1, wherein various levels of a health danger can be displayed by the display device.

9. The system of claim 1, further comprising a transmitter unit, which communicates to a control center at least one selected result of the assessment of a probability of postoperative bleeding or an instruction on how to deal with a momentary condition of the person.

10. The system of claim 9, further comprising a position detector, which identifies a spatial or geographic position of the person.

11. The system of claim 10, wherein the spatial or geographic position of the person is communicated by the transmitter unit to a control room.

12. The system of claim 1, wherein said interface is an interface to a mobile telephone.

13. The system of claim 1, wherein all elements of the system are combined in one unit.

14. The system of claim 1, wherein the person has undergone a tonsillectomy surgery or a thyroid surgery.

15. The system of claim 1, wherein said detector unit records the blood pressure, heart rate, and tissue pressure of the person.

16. The system of claim 1, wherein said detector unit records the blood pressure, heart rate, and oxygen content of the blood of the person.

17. The system of claim 1, wherein said detector unit records the blood pressure, heart rate, tissue pressure, and oxygen content of the blood of the person.

* * * * *